United States Patent
Nakamura et al.

(10) Patent No.: US 10,087,605 B2
(45) Date of Patent: Oct. 2, 2018

(54) OIL PROPERTIES DIAGNOSTIC SYSTEM FOR WORK MACHINE

(71) Applicant: HITACHI CONSTRUCTION MACHINERY CO., LTD., Tokyo (JP)

(72) Inventors: Teruo Nakamura, Toride (JP); Akira Kurasako, Tsuchiura (JP); Hideki Akita, Tsuchiura (JP); Yoshiya Hamamachi, Toride (JP); Katsutoshi Hakozaki, Souka (JP); Kotaro Ogura, Katsushika (JP)

(73) Assignee: Hitachi Construction Machinery Co., Ltd., Tokyo (JP)

( * ) Notice: Subject to any disclaimer, the term of this patent is extended or adjusted under 35 U.S.C. 154(b) by 0 days.

(21) Appl. No.: 15/509,508

(22) PCT Filed: Oct. 20, 2015

(86) PCT No.: PCT/JP2015/079614
§ 371 (c)(1),
(2) Date: Mar. 8, 2017

(87) PCT Pub. No.: WO2016/098440
PCT Pub. Date: Jun. 23, 2016

(65) Prior Publication Data
US 2017/0284068 A1 Oct. 5, 2017

(30) Foreign Application Priority Data
Dec. 15, 2014 (JP) .................................. 2014-253524

(51) Int. Cl.
*E02F 9/26* (2006.01)
*G01N 33/30* (2006.01)
*G07C 5/00* (2006.01)

(52) U.S. Cl.
CPC ............... *E02F 9/26* (2013.01); *G01N 33/30* (2013.01); *G07C 5/004* (2013.01)

(58) Field of Classification Search
CPC ............. E02F 9/26; G07C 5/004; G01N 33/30
See application file for complete search history.

(56) References Cited

U.S. PATENT DOCUMENTS 5,887,365 A * 3/1999 Fujishima ............... E02F 3/437
37/348
6,882,961 B2 * 4/2005 Cobble ..................... E02F 9/26
700/104

(Continued)

FOREIGN PATENT DOCUMENTS

| JP | 58-171647 A | 10/1983 |
| JP | 58-201047 A | 11/1983 |

(Continued)

OTHER PUBLICATIONS

International Preliminary Report on Patentability received in corresponding International Application No. PCT/JP2015/079614 dated Jun. 29, 2017.

(Continued)

*Primary Examiner* — Frederick M Brushaber
(74) *Attorney, Agent, or Firm* — Mattingly & Malur, PC

(57) ABSTRACT

A diagnostic system for a work machine includes a data storage device (210) in which sensor information (A) input from a sensor (101A) that senses an oil property of oil used for operation of the work machine and an abnormality degree determination value defined for each kind of the sensor information (A) are stored, and an arithmetic processing device (104) that executes first processing of discriminating the degree of abnormality level of the oil based on the sensor information (A) and the abnormality degree determination value, second processing of determining whether or not necessity to carry out oil analysis involving (Continued)

oil extraction exists based on the degree of abnormality level of the oil discriminated in the first processing, and third processing of outputting information indicating that the oil analysis is necessary to other terminal if it is determined that the oil analysis is necessary in the second processing.

5 Claims, 10 Drawing Sheets

(56) References Cited

U.S. PATENT DOCUMENTS

| | | | | |
|---|---|---|---|---|
| 6,907,384 B2 * | 6/2005 | Adachi | ............ | E02F 9/205 701/50 |
| 7,079,982 B2 * | 7/2006 | Ogura | ............ | E02F 9/205 702/185 |
| 7,228,505 B2 * | 6/2007 | Shimazu | ............ | B60K 37/02 701/29.1 |
| 7,410,446 B2 * | 8/2008 | DeMarco | ............ | B60W 30/194 477/98 |
| 8,791,803 B2 * | 7/2014 | Ishikawa | ............ | G01M 15/042 340/425.5 |
| 2004/0128107 A1 | 7/2004 | Ryu et al. | | |

FOREIGN PATENT DOCUMENTS

| | | |
|---|---|---|
| JP | 61-070208 A | 4/1986 |
| JP | 07-219622 A | 8/1995 |
| JP | 2002-173954 A | 6/2002 |
| JP | 2004-211884 A | 7/2004 |

OTHER PUBLICATIONS

International Search Report of PCT/JP2015/079614 dated Dec. 28, 2015.

* cited by examiner

OIL PROPERTIES DIAGNOSTIC SYSTEM FOR WORK MACHINE

TECHNICAL FIELD

The present invention relates to a system for diagnosing properties of oil used for a work machine.

BACKGROUND ART

In recent years, there have been made attempts to apply, to work machines, comprehensive abnormality diagnosis in which the result of an oil analysis by human hand or the result of visual determination is added to information on sensed values of various kinds of sensors provided in the work machines including hydraulic excavators, dump trucks, wheel loaders, forklifts, cranes, and so forth.

For example, in Patent Document 1, a system is disclosed that discriminates the abnormality level of a construction machine based on a combination of all or any two pieces of first construction machine information sensed and collected by a sensor group (for example, sensors of engine revolution speed, engine hydraulic pressure, oil temperature, and blow-by pressure) provided in the construction machine, second construction machine information collected by analyzing oil extracted from the construction machine by a serviceman (oil analysis information), and third construction machine information collected through visual determination of the construction machine by a serviceman (visual information).

PRIOR ART DOCUMENT

Patent Document

Patent document 1: JP-2002-173954-A

SUMMARY OF THE INVENTION

Problems to be Solved by the Invention

The work machine is frequently required to stably operate in order to observe a construction period planned in advance. For this reason, the work machine is required to have a function of predictive diagnosis to sense an abnormal state at a stage before the occurrence of an abnormality such as a breakdown and prevent the occurrence of downtime due to a sudden breakdown or the like as much as possible. Furthermore, the work machine is frequently provided with an attachment fit for a work site or tuning fit for the required performance, and it is difficult to easily deploy an alternative work machine at the time of occurrence of a breakdown. From this point, it is desired to prevent the occurrence of downtime.

Moreover, the work machine is an expensive product and expensive objects are often included in parts thereof. For increasing needs for resource saving, it is also required that parts of an engine system and a hydraulic equipment system, which are core parts of the work machine, be reused as reworked parts through applying of proper repair after being once used. For this purpose, it is important to carry out proper maintenance at proper timing so that the parts may be prevented from deteriorating to such an extent that the rework is impossible.

Therefore, by accurately grasping an abnormal state early as a predictive phenomenon of a breakdown or the like that occurs in a work machine and intending an early arrangement for replacement parts and sensing of the abnormal state at an early stage or reuse of parts for promoting reduction in the repair cost, reduction in the expenses for services and the parts replacement cost as the total lifecycle cost needs to be achieved and the utilization rate itself of the work machine at a construction site, a work site, or the like also needs to be improved.

So, development is being advanced on abnormality diagnosis techniques, typified by the technique of the above-described document, in which the operating status of a work machine ("first construction machine information" in the above-described document) is measured by using various kinds of sensors provided in the work machine and whether an abnormality exists is monitored. Meanwhile, for core parts of an engine system and a hydraulic equipment system of the work machine, in addition to the abnormality diagnosis techniques based on sensor information, a method has been proposed in which a person in charge of services goes off to a work site and extracts oil used for the core parts (engine oil, hydraulic operating fluid, and so forth) at a periodic time interval. The extracted oil is analyzed in detail in an oil analysis center. The oil analysis result is utilized with the measurement values of the above-described respective kinds of sensors for status monitoring about whether or not an abnormality exists in the core parts of the work machine, through comparison with the past oil analysis result and so forth.

However, in this method, the person in charge of services needs to periodically go off to a work site and extract oil from plural core parts, and the work is troublesome. Furthermore, the work machine needs to be stopped during the oil extraction and thus the work efficiency decreases. Moreover, although the extracted oil is analyzed, the state of the work machine is determined to be normal in many cases. Therefore, there is a tendency that incentive works in such a direction as to extend the interval of the oil extraction as much as possible and minimize downtime accompanying the oil extraction (such a direction as to maximize the work efficiency of the work machine). On the other hand, if the interval of the oil extraction is set too long, even when an abnormality is not found in machine information sensed and collected by the sensor group provided in the work machine (first construction machine information), oil deteriorates and the lubrication performance is lowered, and it is also possible that abnormal wear of parts progresses by the time of the next oil extraction and damage progresses to such an extent that repair is difficult. Due to this, there is a possibility that the case in which a used part cannot be utilized as a reworked part also arises.

The present invention is made in view of the above circumstances and an object thereof is to provide a diagnostic system for a work machine that can accurately determine whether or not the necessity for detailed oil analysis involving oil extraction exits.

Means to Solve the Problems

The present application includes plural means to solve the above-described problems. To cite one example thereof, a diagnostic system for a work machine includes a data storage device in which at least one piece of sensor information input from at least one sensor that senses at least one oil property about oil used for operation of the work machine and a determination value defined as at least one determination value for each kind of the sensor information are stored, and an arithmetic processing device that executes first processing of discriminating the degree of abnormality level of the oil based on the at least one piece of sensor information and the determination value relating to the at least one piece of sensor information, second processing of determining whether or not necessity to carry out oil analysis involving oil extraction exists based on the degree of abnormality level of the oil discriminated in the first processing, and third processing of outputting information indicating that the oil analysis involving oil extraction is necessary to other terminal if it is determined that the oil analysis involving oil extraction is necessary in the second processing.

Effect of the Invention

According to the present invention, whether or not the necessity for detailed oil analysis involving oil extraction exists can be accurately determined based on the information output from the sensor that can directly sense the state of the oil property. Thus, optimization of the oil extraction timing and minimization of downtime of the work machine can be achieved.

MODES FOR CARRYING OUT THE INVENTION

In engines mounted in work machines typified by hydraulic excavators and pieces of hydraulic equipment such as hydraulic pumps and hydraulic cylinders, properties themselves of oil (engine oil and hydraulic operating fluid) used as a medium for lubrication of parts or power transmission deteriorate due to repetition of high load operation such as excavation. Furthermore, in association with the deterioration of the lubrication performance of these kinds of oil, trouble such as wear occurs at the contact part of parts that receive the high load. To enhance the durability of the engine and parts of the hydraulic equipment system, the oil needs to be periodically replaced to keep the lubrication performance of the oil appropriate. Furthermore, the cleanliness of the oil is kept from fine wear debris and so forth generated on the contact surfaces inside parts due to the high load operation, through a filter provided in a return circuit of the oil. However, wear damage is accumulated also in the filter itself in association with the deterioration of oil properties and thus periodic replacement is necessary likewise. Furthermore, when damage such as wear of a part becomes large, the part itself needs to be replaced.

A diagnostic system for a work machine according to the present embodiment is constructed in view of such a background and senses the states of properties of oil used as a medium for lubrication or power transmission for core parts of an engine system and a hydraulic equipment system of the work machine by sensors. Furthermore, the diagnostic system discriminates the degree of abnormality level of the oil in real time based on pieces of sensor information thereof (numerical values representing the physical and chemical states of the oil) and prompts oil extraction for detailed oil analysis at proper timing before the work machine reaches a breakdown according to the discrimination result. Due to this, breakdowns can be prevented by carrying out appropriate oil replacement, filter replacement, part replacement, or the like and the work machine can be efficiently managed by rapidly carrying out response handling such as repair. Moreover, it becomes easy to carry out rework handling for parts and therefore it becomes easy to recover the performance of these parts.

In the following, description will be made by taking an embodiment that utilizes a hydraulic excavator as an example. However, techniques of the present invention can be applied to not only hydraulic excavators but also other work machines such as dump trucks, wheel loaders, bulldozers, forklifts, and cranes as long as they are work machines that use oil as a lubricant or a power transmission medium.

Figure 1:
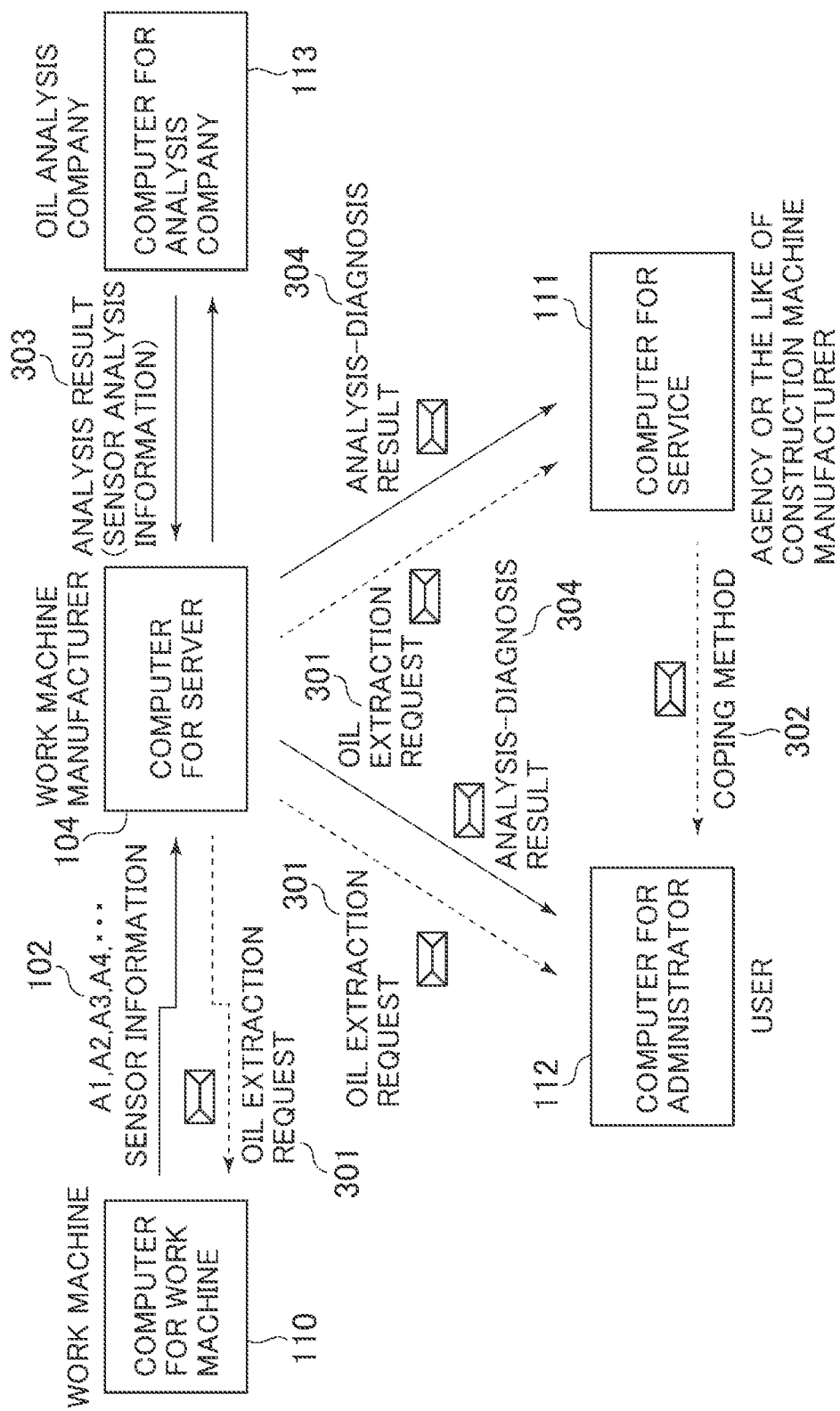
FIG. 1 is a schematic configuration diagram of a diagnostic system for a work machine according to an embodiment of the present invention.

FIG. 1 is a schematic configuration diagram of a diagnostic system for a work machine according to an embodiment of the present invention. The diagnostic system shown in this diagram includes a computer (computer for a work machine) 110 mounted in a hydraulic excavator 501 (see FIG. 2), a computer 104 for a server under management by a manufacturer that has manufactured the hydraulic excavator 501, a computer (computer for an administrator) 112 used by an administrator (user) of the hydraulic excavator 501, a computer (computer for services) 111 used by a person in charge of services (serviceman) that belongs to a work machine manufacturer or a sales office, an agency or the like thereof and carries out breakdown repair and maintenance of the hydraulic excavator 501, and a computer 113 for an analysis company under management by an oil analysis company that analyses oil extracted from the hydraulic excavator 501.

Although description is not made with diagrammatic representation, the respective computers 110, 104, 112, 111, and 113 include an arithmetic processing device (for example, CPU) as arithmetic means for executing various kinds of programs, a data storage device (for example, semiconductor memories such as a read only memory (ROM), a random access memory (RAM), and a flash memory and a magnetic data storage device such as a hard disk drive) as storing means for storing various kinds of data typified by these programs, and an input-output arithmetic processing device for carrying out input-output control of data, instructions, and so forth to and from the arithmetic processing device, the data storage device, and so forth. Moreover, a display device (for example, liquid crystal monitor) for displaying a processing result and so forth by the arithmetic processing device may be included if information provision to a person typified by an operator of the computer is necessary. Furthermore, as the respective computers 104, 110, 111, 112, and 113 that form the present diagnostic system, not only stationary terminals but also portable terminals (mobile phones, smartphones, tablet terminals, and so forth) can be used.

Figure 2:
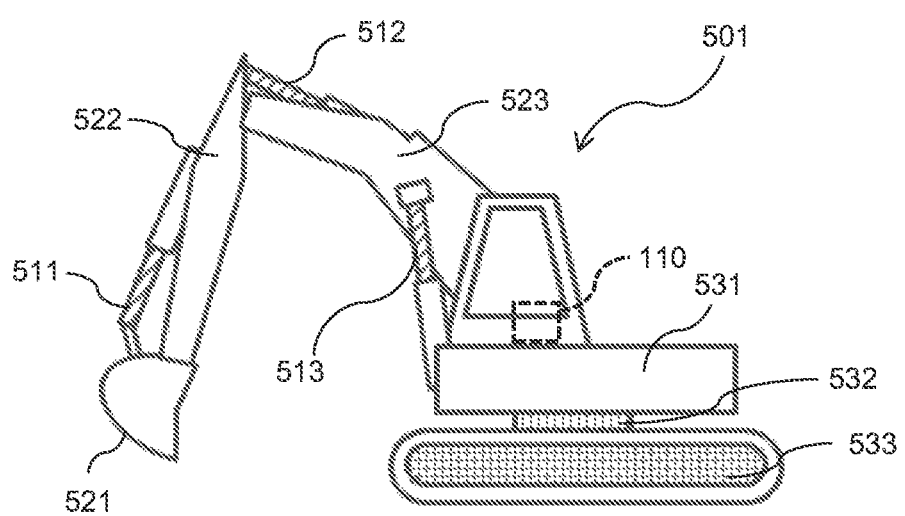
FIG. 2 is an overall configuration diagram of a hydraulic excavator 501.

FIG. 2 shows the overall configuration diagram of the hydraulic excavator 501. The hydraulic excavator 501 includes oil property sensors 101A, 101B, and 101C (shown in FIG. 3 and FIG. 4), the computer 110 for the work machine, hydraulic cylinders 511, 512, and 513 for driving a bucket 521, an arm 522, and a boom 523, a hydraulic pump 602 (see FIG. 3) that supplies a hydraulic operating fluid to the respective hydraulic actuators in the hydraulic excavator, typified by the hydraulic cylinders 511, 512, and 513, an engine 601 (see FIG. 3) that drives the hydraulic pump 602, a lower track structure 533 having a crawler (endless track) driven by a hydraulic motor (not shown), and an upper swing structure 531 that is swingably attached to the upper part of the lower track structure 533 with the intermediary of a swing mechanism 532 and is driven to swing by a hydraulic motor (not shown).

The operation of the hydraulic excavator 501 will be described. When the hydraulic excavator 501 carries out operation such as excavation, the bucket 521, the arm 522, and the boom 523 are driven by expansion and contraction operation of the hydraulic cylinders 511, 512, and 513. The lower part of the boom 523 is attached to the upper swing structure 531.

Figure 3:
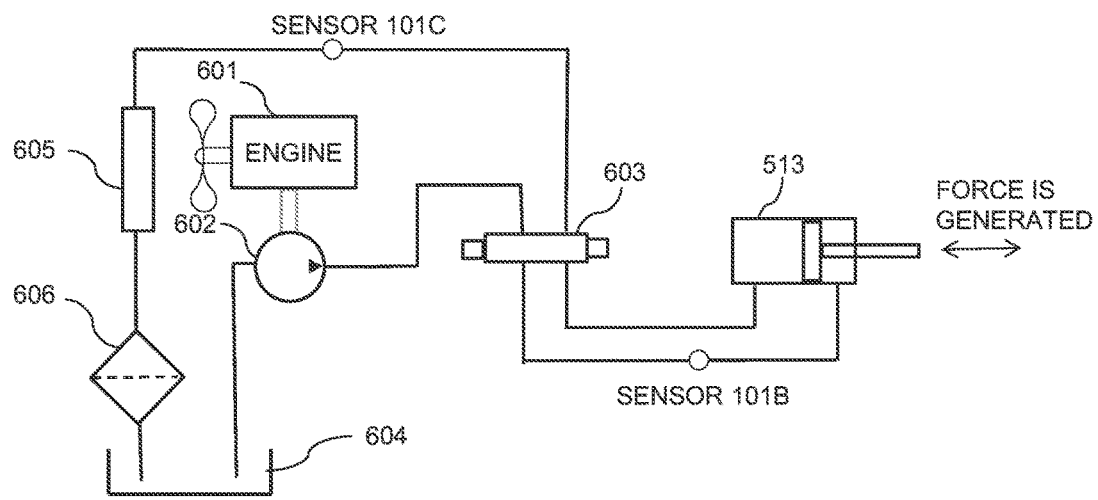
FIG. 3 is one example of the configuration of a hydraulic system that generates a hydraulic pressure in a hydraulic cylinder 513.

In FIG. 3, one example of the configuration of a hydraulic system that generates a hydraulic pressure in the hydraulic cylinder 513 is shown. A hydraulic operating fluid (oil) in a hydraulic operating fluid tank 604 is drawn by the hydraulic pump 602 and is sent to a control valve 603 that controls the flow rate and direction of the hydraulic operating fluid guided to the hydraulic cylinder (boom cylinder) 513 for example. The control valve 603 controls the hydraulic operating fluid according to the switching position thereof and supplies the hydraulic operating fluid to the hydraulic cylinder 513. Thereby, the hydraulic cylinder 513 is driven and the boom 523 operates. Furthermore, the hydraulic operating fluid that flows out from the hydraulic cylinder 513 is led to an oil cooler 605 via the control valve 603 to be cooled, and thereafter is returned to the hydraulic operating fluid tank 604 via a hydraulic operating fluid filter 606.

The oil property sensor 101B is provided in a hydraulic line that connects the control valve 603 and a head-side hydraulic chamber of the hydraulic cylinder 513, and senses at least one of properties (for example, temperature, viscosity, density, dielectric constant, and so forth are included) of the hydraulic operating fluid that passes through this hydraulic line. The oil property sensor 101C is provided in a hydraulic line that connects the control valve 603 and the oil cooler 605, i.e. hydraulic line (return circuit) through which the hydraulic operating fluid passes when returning to the tank 604, or in the tank, and senses at least one of properties of the hydraulic operating fluid that passes through this hydraulic line or in the tank.

Although the configuration of the hydraulic system relating to the boom cylinder 513 is described in FIG. 3, corresponding control valves each exist also regarding other hydraulic actuators and the respective hydraulic actuators are driven as appropriate by hydraulic operating fluids controlled by the respective control valves.

Figure 4:
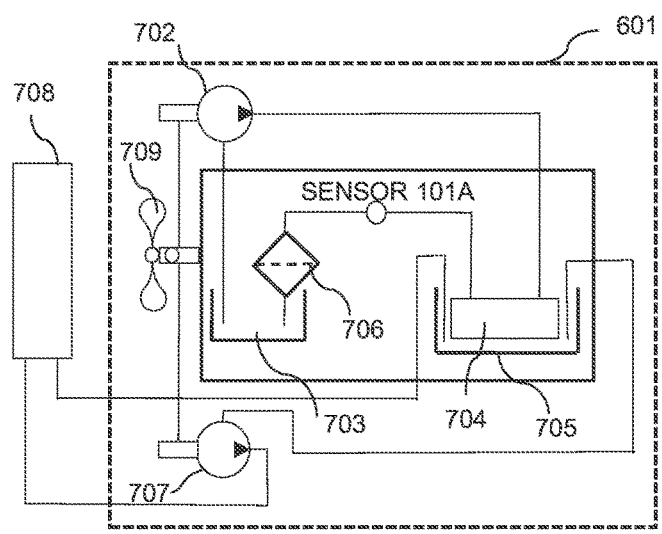
FIG. 4 is a configuration diagram of an oil system of an engine 601 in the hydraulic excavator 501.

FIG. 4 is a configuration diagram of an oil system of the engine 601 in the hydraulic excavator 501. Engine oil is used for lubrication of the inside of the engine 601 and cooling of the engine 601. In FIG. 4, an oil pump 702 is driven in accordance with the revolution of the engine 601. The oil pump 702 sucks the engine oil from an oil pan 703 and sends the engine oil to an oil cooler 704. The engine oil cooled in the oil cooler 704 through heat exchange with cooling water in a water jacket 705 is returned to the oil pan 703 after foreign matters are removed by an oil filter 706.

Furthermore, a water pump 707 is also driven by the revolution of the engine 601 and sucks the cooling water in the water jacket 705 to supply it to a radiator 708. The cooling water cooled by the radiator is returned to the water jacket 705. The radiator 708 is cooled (air-cooled) by air taken in by a cooling fan 709 attached to the revolving part of the engine 601.

The oil property sensor 101A is provided in a hydraulic line (return circuit) that connects the oil cooler 704 and the oil filter 706 and through which the engine oil passes when returning to the oil pan 703, and senses at least one of properties of the engine oil that passes through this hydraulic line.

The respective oil property sensors 101A, 101B, and 101C sense (measure) at least one oil property about the oil used for the operation of the hydraulic excavator 501 (all kinds of oil used in the hydraulic excavator, such as the hydraulic operating fluids of the hydraulic actuators and the engine oil, can be the target) according to the specifications thereof. Sensor signals of the respective oil property sensors 101A, 101B, and 101C are processed as appropriate and are input and stored into the computer 110 for the work machine and the computer 104 for the server as information that indicates the physical quantity of the oil property (referred to as oil property information or sensor information). Although the setting places of only the three oil property sensors 101A, 101B, and 101C are described here for simplification of description, the hydraulic excavator 501 is provided with oil property sensors besides these three sensors and there is no particular limit to the number of sensors. In the following, the plural oil property sensors provided in the hydraulic excavator 501, typified by the three oil property sensors 101A, 101B, and 101C, will be often referred to as a sensor group 101.

As oil properties that should be measured by the oil property sensors 101A, 101B, and 101C, the temperature, viscosity, density, dielectric constant, and so forth of oil exist as basic properties. Furthermore, oil properties such as color information of oil and the contamination class may be added to them as measurement targets according to need. The oil property that can be measured by a respective one of the oil property sensors differs depending on the specifications of the sensor (sensor that can measure not only one oil property but at least two oil properties also exists) and therefore the combination of the oil property sensors actually mounted in the hydraulic excavator 501 differs depending on the oil properties desired to be measured and the specifications of each sensor.

Figure 5:
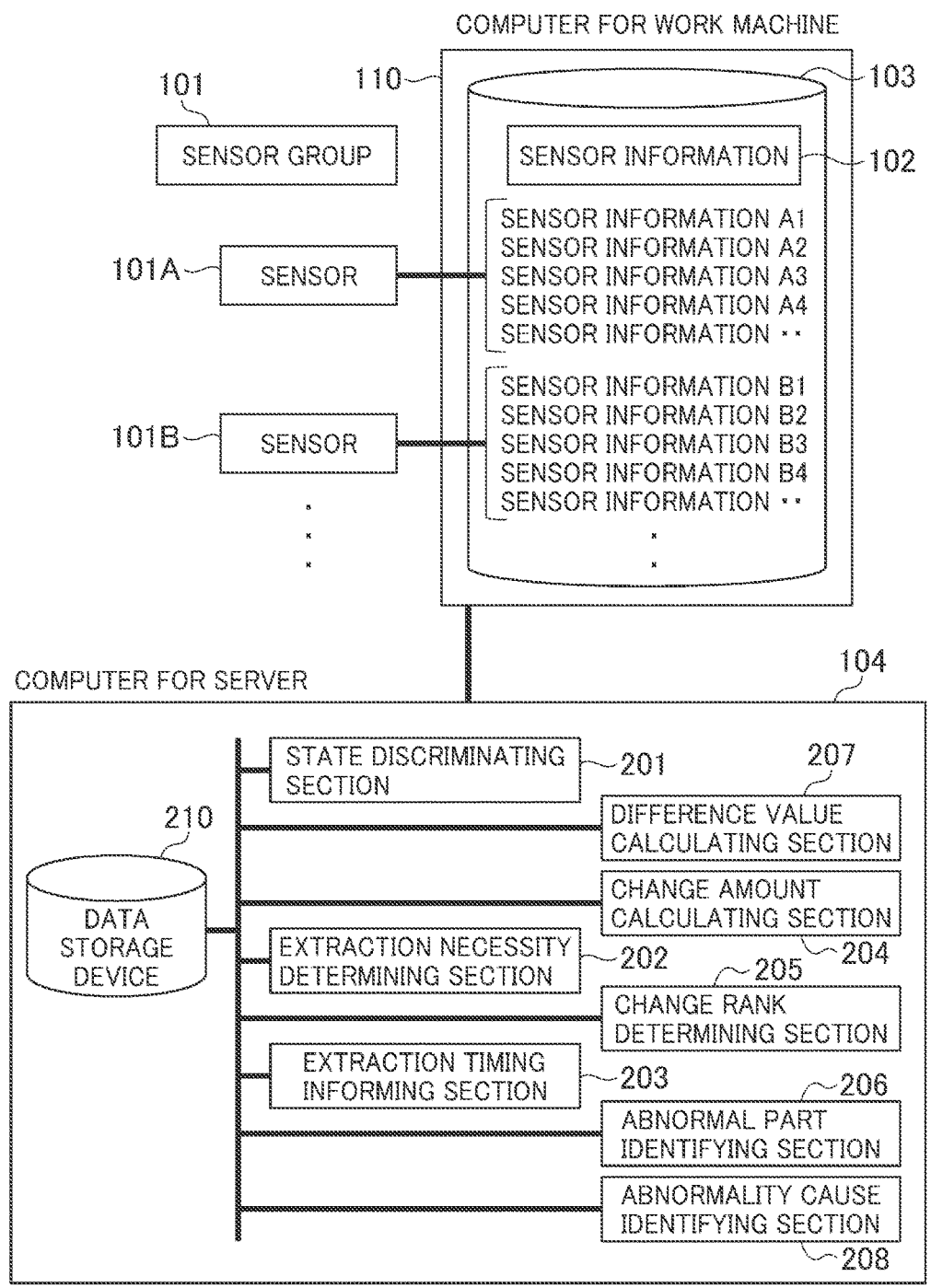
FIG. 5 is a schematic configuration diagram of a computer 110 for a work machine and a computer 104 for a server.

FIG. 5 is a schematic configuration diagram of the computer 110 for the work machine and the computer 104 for the server.

The computer 110 for the work machine includes a data storage device 103 for storing sensor information (sensor information of a first level) 102 input from the sensor group 101 mounted in the hydraulic excavator 501. The three sensors 101A, 101B, and 101C according to the present embodiment can measure a respective one of different oil properties. As shown in FIG. 5, for example, the sensor signal of the sensor 101A at a certain clock time is processed as appropriate in the computer 110 for the work machine and is stored as sensor information A1 in the data storage device 103 of the computer 110 for the work machine while being associated with the measurement clock time. Pieces of sensor information A1, A2, A3, A4 . . . in FIG. 5 represent pieces of sensor information measured by the same sensor 101A at different clock times and the number at the tail end increases over time. Due to this, time-series data of sensor information A of the sensor 101A is stored in the computer 110 for the work machine. This is the same also regarding the other sensors 101B and 101C although description is omitted.

The computer 104 for the server includes a state discriminating section 201 that executes processing (first processing) of discriminating the degree of abnormality level of oil based on certain sensor information (oil property information) and an abnormality degree determination value (described later) relating to the sensor information, an extraction necessity determining section 202 that executes processing (second processing) of determining whether or not the necessity to carry out oil analysis involving oil extraction exists based on the result of the discrimination by the state discriminating section 201, and an extraction timing informing section 203 that executes processing (third processing) of outputting information indicating that the oil analysis involving oil extraction is necessary to other terminals (for example, the computer 111 for the service, the computer 112 for the administrator, and so forth) if it is determined that the oil analysis involving oil extraction is necessary in the extraction necessity determining section 202.

Moreover, the computer 104 for the server includes a change amount calculating section 204 that calculates a change amount that is the difference between the previous value and the present value of certain sensor information, a change rank determining section 205 that classifies the rank of this change amount based on this change amount and a change amount determination value, an abnormal part identifying section 206 that executes processing of identifying a part in which an abnormality has occurred or that has a possibility of the occurrence of an abnormality based on the setting place of the sensor that has output the sensor information as the basis of a determination that the oil analysis involving oil extraction is necessary if the determination is made in the second processing, a difference value calculating section 207 that calculates a difference value between certain sensor information and a predetermined value (for example, initial value of sensor information), and an abnormality cause identifying section 208 that executes processing of identifying the cause of an abnormality of oil based on certain sensor information and past oil analysis information of the oil property relating to this certain sensor information.

The computer 104 for the server is wirelessly connected or connected in a wired manner to the computer 110 for the work machine so that data communications can be mutually carried out. The time-series data of the sensor information (sensor information of the first level) stored in the data storage device 103 of the computer 110 for the work machine is input to the computer 104 for the server and is stored in a data storage device 210 of the computer 104 for the server.

In the data storage device 210 of the computer 104 for the server, thresholds defined for each kind of oil property information are stored in addition to the sensor information acquired by the sensor group 101. For example, if the sensor 101A measures the dielectric constant (sensor information A) and the sensor 101B measures the viscosity (sensor information B) and the sensor 101C measures the density (sensor information C) as the oil property information, thresholds SA, SB, and SC defined for the dielectric constant, the viscosity, and the density, respectively, are stored. The thresholds are utilized for decision of the abnormality degree determination values used in the discrimination of the degree of abnormality level of oil by the state discriminating section 201. In the present embodiment, values obtained by multiplying the respective thresholds by a predetermined percentage are used as the abnormality degree determination values. Specifically, 30% and 50% are used as the predetermined percentages. The abnormality degree determination value obtained by multiplying the threshold by 30% is referred to as a warning determination value and the abnormality degree determination value obtained by multiplying the threshold by 50% is referred to as an abnormality determination value.

If certain sensor information is equal to or larger than 30% of the threshold corresponding thereto and is smaller than 50% (if the certain sensor information is equal to or larger than the warning determination value and is smaller than the abnormality determination value), an abnormality does not exist in oil but the possibility of that an abnormality is recognized in the future is high. So, the state discriminating section 201 discriminates the degree of abnormality level as "warning" in order to call attention to the future change in the sensor information (warning determination). If the certain sensor information is equal to or larger than 50% of the threshold (if the certain sensor information is equal to or larger than the abnormality determination value), the state discriminating section 201 deems that an abnormality is recognized in oil and discriminates the degree as "abnormal" (abnormality determination). If the certain sensor information is smaller than 30% of the threshold (if the certain sensor information is smaller than the warning determination value), the state discriminating section 201 deems that an abnormality is not recognized and discriminates the degree as "normal" (normality determination). Each threshold is defined based on the track record of the correlation between past sensor information (oil property information) acquired by the hydraulic excavator 501 and hydraulic excavators of the same model as the hydraulic excavator 501 and the degree of abnormality level of oil.

Figure 6:
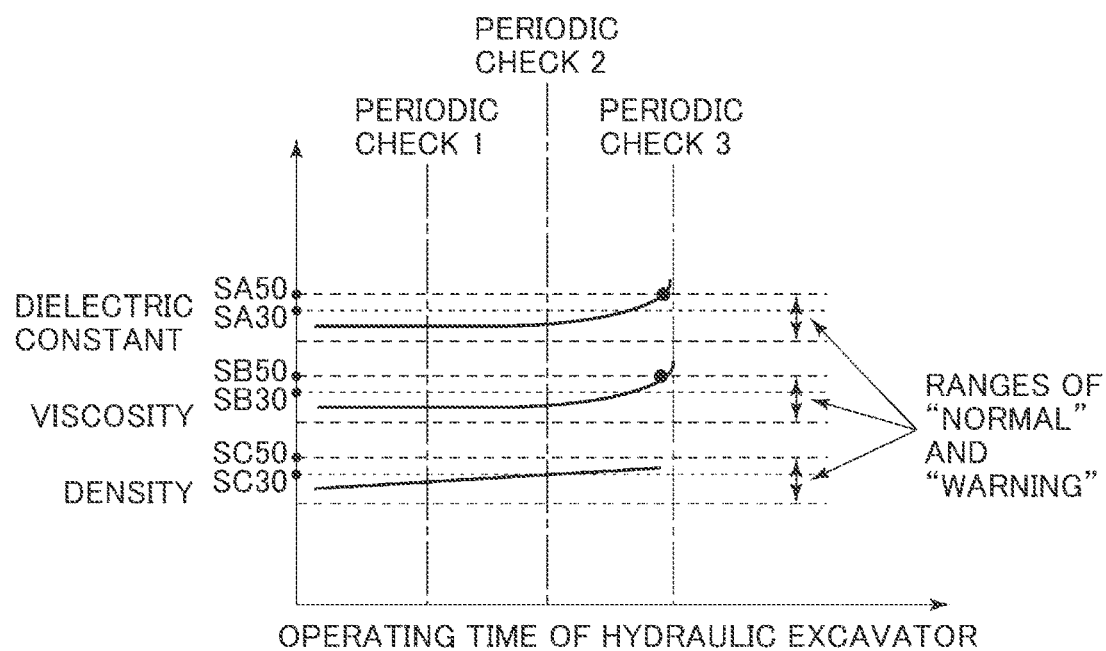
FIG. 6 is a diagram showing time change in each kind of sensor information when a sensor 101A is measuring the dielectric constant and a sensor 101B is measuring the viscosity and a sensor 101C is measuring the density.

FIG. 6 is a diagram showing time change in each kind of sensor information when the sensor 101A is measuring the dielectric constant (sensor information A) and the sensor 101B is measuring the viscosity (sensor information B) and the sensor 101C is measuring the density (sensor information C). In the diagram, the value of 30% of the threshold SA (warning determination value) relating to the dielectric constant is represented as SA30 and the value of 50% (abnormality determination value) is represented as SA50. The value of 30% of the threshold SB (warning determination value) relating to the viscosity is represented as SB30 and the value of 50% (abnormality determination value) is represented as SB50. The value of 30% of the threshold SC (warning determination value) relating to the density is represented as SC30 and the value of 50% (abnormality determination value) is represented as SC50.

The state discriminating section 201 compares the respective pieces of sensor information (oil property information)

acquired by the sensor group 101 with the warning determination values SA30, SB30, and SC30 and the abnormality determination values SA50, SB50, and SC50, and determines which of the three degrees of "normal," "warning," and "abnormal" the degree of abnormality level of oil is.

In the present embodiment, one threshold is set for each kind of sensor information (oil property information) and the degree of abnormality level of oil is determined based on two abnormality degree determination values (warning determination value and abnormality determination value) decided from this threshold. However, at least three abnormality degree determination values may be set and the degree of abnormality level may be classified more finely. Furthermore, instead of deciding plural abnormality degree determination values with the intermediary of the threshold, plural abnormality degree determination values may be directly decided without the intermediary of the threshold and the degree of abnormality level may be classified.

If plural abnormality degree determination values are defined by deciding plural percentages with respect to one threshold as described above, the respective abnormality degree determination values can be easily changed only by changing the numerical values of these percentages. Although the degree of importance and so forth of the work machine frequently differ depending on the user, allowing the abnormality degree determination values to be easily changed as above makes it easy to manage the work machine in accordance with the preference of the user.

Figure 7:
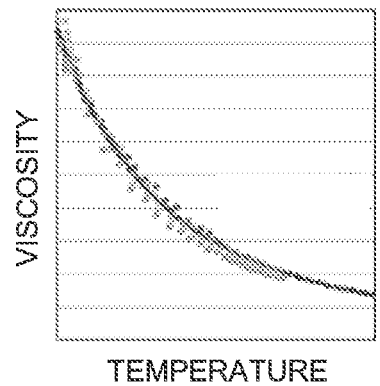
FIG. 7 is a diagram showing the correlation between the viscosity (one example of oil properties sensed in a sensor group 101) and the temperature.

FIG. 7 is a diagram showing the correlation between the viscosity, which is one of oil properties, and the temperature. From this diagram, it turns out that the viscosity is a temperature-dependent characteristic value that changes with temperature change. In the oil properties sensed by the sensor group 101, not only the viscosity of FIG. 7 but temperature-dependent ones are included. So, the state discriminating section 201 in the present embodiment transforms a measurement value (sensor information) $X_i(t)$ of each oil property at an arbitrary temperature t into the format of the following cubic polynomial (expression 1) before carrying out comparison with the warning determination value and the abnormality determination value. This can transform the measurement value (sensor information) into a value in a predetermined temperature range with accuracy that is significant in practical use, and can transform the measurement value into a value in a temperature range assumed by the threshold as the basis of the abnormality degree determination value (warning determination value and abnormality determination value) for example. The state discriminating section 201 discriminates the degree of abnormality level of oil by comparing the value $X_i(t)$ after the transform by expression 1 and the warning determination value and the abnormality determination value. Suffix i in the following expression is an integer equal to or larger than 1 and represents the kind of oil property. For example, it can be subscribed that the viscosity is $X_1$ and the density is $X_2$ and the dielectric constant is $X_3$. Furthermore, $b_{0i}$, $b_{1i}$, $b_{2i}$, and $b_{3i}$ in the following expression are coefficients.

$$X_i(t)=b_{0i}+b_{1i} \cdot t+b_{2i} \cdot t^2+b_{3i} \cdot t^3 \quad \text{(expression 1)}$$

Furthermore, as for the sensor information of oil properties that do not depend on the temperature comparatively (for example, color information, contamination class), the measurement value can be expressed in the form of expression 1 similarly to temperature-dependent properties by adjusting the coefficients of the second and subsequent terms of the above-described expression 1.

Next, the extraction necessity determining section 202 will be described. The extraction necessity determining section 202 determines that "necessity exists" for oil analysis involving oil extraction if the degree of abnormality level is discriminated as "abnormal" in the state discriminating section 201. The extraction necessity determining section 202 determines that "necessity does not exist" if the degree is discriminated as "normal." Furthermore, if the degree is discriminated as "warning" in the state discriminating section 201, the state discriminating section 201 determines whether or not the necessity for oil extraction exists based on whether it is possible to postpone the timing of oil extraction to a periodic oil replacement timing (periodic replacement timing). Next, the processing of the extraction necessity determining section 202 when the degree is discriminated as "warning" will be described in detail.

In the determination of whether or not the necessity for oil extraction exists when the degree of abnormality level of oil is "warning," the extraction necessity determining section 202 executes processing of determining whether or not the necessity to carry out oil analysis involving oil extraction by the time of the next oil replacement exists by determining whether or not the abnormality level of oil progresses to "abnormal" even when the hydraulic excavator 501 is operated until the time of the next oil replacement based on the sensor information selected by the state discriminating section 201 and the time change rate of this sensor information. More specifically, first the extraction necessity determining section 202 compares a time T1 from the measurement clock time relating to the relevant sensor information to the next periodic oil replacement timing and a time T2 that is the time required for this sensor information to reach the abnormality determination value from the measurement clock time relating to this sensor information and is estimated from the time change rate of this sensor information. Then, if T2 is longer than T1, the extraction necessity determining section 202 deems that the abnormality level of oil is not "abnormal" also at the time of the next periodic oil replacement, and takes this to mean that it suffices to carry out the oil analysis involving oil extraction at the time of this periodic oil replacement. So, the extraction necessity determining section 202 determines that "necessity does not exist" for the oil analysis involving oil extraction. On the other hand, if T2 is equal to or shorter than T1, the extraction necessity determining section 202 deems that the abnormality level of oil has already reached "abnormal" at the time of the next periodic oil replacement timing, and determines that "necessity exists" for the oil analysis involving oil extraction.

Next, the extraction timing informing section 203 will be described. If it is determined that "necessity exists" for the oil analysis involving oil extraction in the extraction necessity determining section 202, the extraction timing informing section 203 outputs information indicating this as an oil extraction request 301 to at least one of the computer 110 for the work machine, the computer 112 for the administrator, and the computer 111 for services and informs related persons of the hydraulic excavator 501 to that effect so that the oil may be extracted as immediately as possible and detailed oil analysis may be carried out in the oil analysis company. The oil extraction request 301 may be transmitted also to the computer 113 for the oil analysis company. On the other hand, if it is determined that "necessity does not exist," the extraction timing informing section 203 does not output the oil extraction request 301.

First Embodiment

Figure 8:
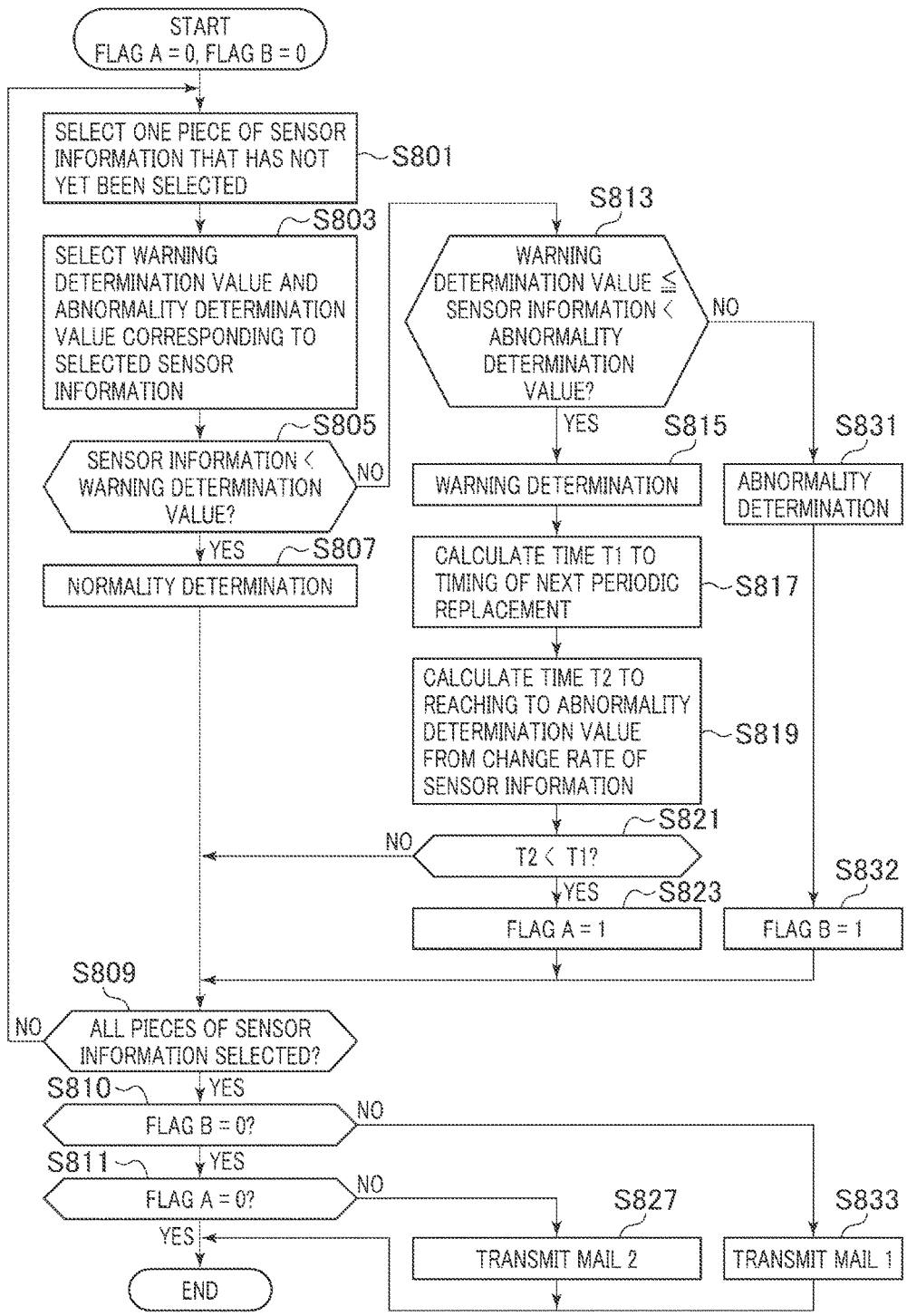
FIG. 8 is one example of a flowchart of processing executed by the computer 110 for the server in a first embodiment.

Next, one example of a series of processing executed by the diagnostic system configured as above will be described by using FIG. 8. FIG. 8 is one example of the flowchart of processing executed by the computer 104 for the server in a first embodiment.

The computer 104 for the server calls the processing of the flowchart of FIG. 8 at a predetermined time interval (call cycle). For example, the computer 104 for the server calls the processing at the time of engine start-up and thereafter calls the processing at the predetermined time interval (for example, one hour interval) until the time of engine stop. Furthermore, the computer 104 for the server resets flags A and B to set them to zero (deactivate flags A and B) at the time of each call (at each start of the flowchart), and collects pieces of sensor information of the respective oil properties measured at the time of the call and sets all of them to the state of being "not yet selected." In the collection of the sensor information, as for the oil property that does not have the sensor information measured at the time of the call, sensor information measured at a timing immediately previous to the timing of the call is collected instead. The timing of acquisition of the sensor information may be made to synchronize with the timing of the call.

In S801, the state discriminating section 201 selects one piece of sensor information that has not yet been selected among the plural pieces of sensor information collected at the start of the flowchart. At this time, the state discriminating section 201 adds a transform to the selected sensor information by using the temperature t of oil at the time of measurement of the selected sensor information and (expression 1).

In S803, the state discriminating section 201 selects the threshold corresponding to the sensor information selected in S801 and acquires the warning determination value and the abnormality determination value from the threshold. Then, the state discriminating section 201 discriminates the degree of abnormality level of oil by comparing the warning determination value and the abnormality determination value with the sensor information transformed in S801.

If the sensor information selected and transformed in S801 is determined to be larger than the warning determination value in S805 and furthermore is determined to be larger than the abnormality determination value in S813, transition to S831 is made. That is, when the sensor information selected and transformed in S801 is determined to be equal to or larger than the abnormality determination value, the state discriminating section 201 determines that the degree of abnormality level is "abnormal" (S831), and the extraction necessity determining section 202 determines that the necessity to carry out oil analysis involving oil extraction exists. Then, the extraction necessity determining section 202 activates flag B of abnormality determination (sets flag B=1) in the subsequent S832 and makes transition to S809.

As is apparent from the above, if flag B is 1, this indicates that "the abnormality determination is made and the sensor information regarding which it is determined that oil extraction is "necessary" exists."

On the other hand, when, in S813, the sensor information selected and transformed in S801 is equal to or larger than the warning determination value and is smaller than the abnormality determination value (S813), the state discriminating section 201 determines that the degree of abnormality level is "warning" (S815). Then, the extraction necessity determining section 202 calculates the time T1 from the measurement clock time of the sensor information selected in S801 to the timing of the next oil periodic replacement and calculates the time T2 to the reaching of this sensor information to the abnormality determination value from the time change rate of this sensor information. Then, the extraction necessity determining section 202 compares the magnitude of both (T1 and T2) and determines whether or not the necessity for oil extraction exists (S817, S819, and S821). A concrete example of this processing will be described below.

The periodic replacement timing of oil is prescribed based on a predetermined time interval based on the past track record. Here, for explanation, suppose that the periodic replacement timing of oil is set based on an interval t1 (t1=500 hours) of the operating time of the hydraulic excavator 501.

Here, as "the time T1 to the timing of the next oil periodic replacement" calculated in S817, the number d1 of remaining days to the next periodic replacement is used (T1=d1). In this case, first, "an average operating time t2 of the hydraulic excavator 501 per one day" is calculated from the history of the operating time of the hydraulic excavator 501 stored in the data storage device 210 of the computer 104 for the server. Next, "an operating time t3 of the hydraulic excavator 501 from the timing of the previous periodic replacement to the clock time when the warning determination is made" is subtracted from "the interval t1 of the periodic replacement," and the difference is divided by "the average operating time t2 per one day" and thereby "the number d1 of remaining days to the next periodic replacement" is calculated. For example, in the case in which oil replacement is carried out at intervals of 500 hours (t1=500 hours), if "warning determination" is made at the elapse of 350 hours after the previous replacement (t3=350 hours), assuming that the average operating time per one day is 5 hours (t2=5 hours), the number d1 of days to the next periodic oil replacement is "d1=(500 hours−350 hours)÷5 hours=30 days."

Next, in S819, as "the time T2 to the reaching of the sensor information to the abnormality determination value," the number d2 of remaining days from the measurement clock time of the sensor information selected in S801 (date when the "warning determination" is made) to the reaching of this sensor information to the abnormality determination value is used (T2=d2). Here, with an assumption that the warning determination value is 30% of the threshold and the abnormality determination value is 50% of the threshold, two kinds of cases, the case in which the time change rate of the sensor information per one day is 1% (case 1) and the case in which the time change rate is 0.5% (case 2), are assumed. First, in the case of case 1, the number d2 of days to the reaching to the abnormality determination value from the warning determination value is calculated as "d2=(50%−30%)÷1%=20 days." Furthermore, in the case of case 2, the number d2 of days is calculated as "d2=(50%−30%)÷0.5%=40 days."

Therefore, in the determination of S821 in the case of case 1, "T2=d2=20 days<T1=d1=30 days" is obtained and the extraction necessity determining section 202 determines that oil analysis involving oil extraction is "necessary." Then, the extraction necessity determining section 202 activates flag A in S823 (sets flag A=1 (if flag A=1 has been already set, it is left as it is)) and the processing proceeds to S809. Conversely, in the determination of S821 in the case of case 2, "T2=d2=40 days≥T1=d1=30 days" is obtained and the extraction necessity determining section 202 determines that oil analysis involving oil extraction is "unnecessary," and the processing proceeds to S809.

As is apparent from the above, if flag A is 1, this indicates that "the warning determination is made and the sensor information regarding which it is determined that oil extraction is "necessary" exists."

Furthermore, when, in S805, the sensor information selected and transformed in S801 is smaller than the warning determination value (S805), the state discriminating section 201 determines that the degree of abnormality level is "normal" (S807) and the extraction necessity determining section 202 determines that detailed oil analysis involving oil extraction at this timing is unnecessary, so that the processing proceeds to S809.

In S809, it is determined whether or not all pieces of sensor information have been selected. If sensor information that has not yet been selected exists, the processing returns to S801. On the other hand, if all pieces of sensor information have been selected, transition to S810 is made and the extraction timing informing section 203 checks flag B.

If it proves that 1 is set in flag B in the check of flag B in S810, the extraction timing informing section 203 transmits electronic mail 1 as the oil extraction request 301 to the computer 112 for the administrator and the computer 111 for services (S833). Upon the end of S833, the series of processing shown in FIG. 8 is ended and the computer 104 for the server waits until the next processing start clock time.

In electronic mail 1 in S833, a message to prompt execution of detailed oil analysis involving oil extraction (for example, message of "Please carry out oil extraction and check as soon as possible") is described. Moreover, in addition to this message, identification information (for example, model name or serial number) of the hydraulic excavator as the target of the oil extraction, the operating time (hour meter) of the hydraulic excavator, the clock time when the "abnormality determination" is made (determination clock time), and so forth may be included. The description contents of electronic mail 1 do not need to be common to the computer 112 for the administrator and the computer 111 for services and may be made different depending on the position/role of the transmission destination. Furthermore, instead of the electronic mail, a dedicated application may be automatically activated and similar contents may be displayed on the application. For example, a dedicated informing system may be operated through lighting of a warning lamp that prompts oil extraction in the cab of the hydraulic excavator 501, or the like.

If it proves that 0 is set in flag B in the check of flag B in S810, subsequently the extraction timing informing section 203 checks flag A (S811). If it proves that 1 is set in flag A in this check, the processing proceeds to S827 and the extraction timing informing section 203 transmits electronic mail 2 as the oil extraction request 301 to the computer 112 for the administrator and the computer 111 for services.

In electronic mail 2, a message that clearly shows that the abnormality level of oil reaches the level of an abnormality in the period to the next oil periodic replacement and therefore oil replacement needs to be urgently carried out before the periodic replacement (for example, "Please pay attention to the future determination of the sensor output result because the abnormality level of oil has surpassed the warning determination level") is described.

The contents of electronic mail 1 and electronic mail 2 may be the same or may be made different. In the latter case, that currently the abnormality level is not at the level of an abnormality, the date on which the abnormality level is predicted to reach an abnormality (predicted date), the number of remaining days to this predicted date, a message that prompts execution of oil analysis involving oil extraction by this predicted date, and so forth may be described. Furthermore, although the configuration in which electronic mail 1 is transmitted with priority if both of flags A and B are 1 is employed in the above description, a configuration in which both of electronic mail 1 and electronic mail 2 are transmitted if both of flags A and B are 1 may be employed.

If it proves that 0 is set in flag A in the check of flag A in S811, the series of processing shown in FIG. 8 is ended and the computer 104 for the server waits until the next processing start clock time. Although the processing is ended with a determination that an abnormality is not found particularly if it proves that 0 is set in flag A in S811, a report indicating that the degree of abnormality level is normal may be made by electronic mail or the like.

A user or a person in charge of services who has received the above-described electronic mail 1 (oil extraction request 301) or electronic mail 2 (oil extraction request 301) by the computer 111 or 112 immediately extracts oil from the hydraulic excavator 501 and requests the oil analysis company to analyze the oil. The oil analysis company carries out detailed oil analysis based on the extracted oil and transmits an analysis result 303 (see FIG. 1) thereof from the computer 113 for the analysis company to the computer 104 for the server (work machine manufacturer). In the analysis result 303, information obtained by analyzing the extracted oil in detail regarding the respective oil properties acquired by the sensor group 101 (oil analysis information (referred to also as "sensor information of a second level")) is included. This oil analysis information is sequentially accumulated in the data storage device 210 of the computer 104 for the server. The oil analysis company may transmit, together with the analysis result 303, a diagnosis result 304 based on this analysis result to the computer 104 for the server.

The work machine manufacturer that has received the analysis result 303 makes a diagnosis as appropriate based on this analysis result. Then, the work machine manufacturer transmits the analysis-diagnosis result 304 and a manual for responding thereto (response manual) to the computer 111 for services and transmits this analysis-diagnosis result 304 to the computer 112 for the administrator. The person in charge of services who has received this response manual goes off to the location of the hydraulic excavator 501 and carries out maintenance of the hydraulic excavator 501 based on this response manual. As this maintenance, oil replacement, oil filter replacement, check and replacement of parts, and so forth are included. In the case of maintenance that can be handled on the user side, the person in charge of services may send the coping method by electronic mail 302 (see FIG. 1) or the like and entrust the maintenance to the user instead of going off for the maintenance. Although the case in which communications among the respective parties are carried out by electronic mail is described here, another kind of means can replace the electronic mail as long as it is communication means excellent in the immediacy, such as a FAX, phone, or video phone call. Furthermore, although here the description is made based on the premise that a user or a person in charge of services carries out the oil extraction, the oil analysis company may carry out the oil extraction.

By the way, in the flowchart shown in FIG. 8, the configuration is made in such a manner that the discrimination processing of the abnormality level is repeated until the abnormality level of all pieces of sensor information is determined. If the abnormality level of all pieces of sensor information is acquired in this manner, it becomes possible to know what determination is made on which kind of sensor information. Furthermore, the computer 104 for the server may include the abnormal part identifying section 206 (see FIG. 5) that executes processing of identifying a part in which an abnormality exists based on the setting place of the sensor that has output the sensor information (oil property information) as the basis of a determination that oil analysis involving oil extraction is necessary if the determination is made in the second processing. The inclusion of the abnormal part identifying section 206 can identify the part that should be checked at the time of occurrence of an abnormality. This can achieve efficiency improvement and speeding-up relating to maintenance services through efficiency improvement of check work itself and enabling replacement parts or the like to be prepared in advance according to the degree of abnormality level, and so forth. Thus, it becomes possible to shorten downtime of the work machine as much as possible.

Furthermore, in the example of the flowchart of FIG. 8, which kind of oil should be extracted (in the case of electronic mail 2, which kind of oil has the sensor output result to which attention should be paid) is not described in electronic mail 1. However, which kind of oil needs to be extracted (or which kind of oil has the sensor output result to which attention should be paid) may be determined based on which kind of oil is the sensing target of the sensor that has output the sensor information as grounds for the transmission of electronic mail 1 (or electronic mail 2), and the information thereon may be described in electronic mail. For example, if a determination that extraction of the hydraulic operating fluid is necessary is made, electronic mail 1 in which a message of "Please extract and check the hydraulic operating fluid as soon as possible" is described is transmitted. Furthermore, the configuration may be made in such a manner that both of electronic mail 1 and electronic mail 2 are transmitted when a determination that extraction of certain oil (for example, hydraulic operating fluid) is necessary and a determination that attention needs to be paid to the sensor output result of another kind of oil (for example, engine oil) are made. Alternatively, the configuration may be made in such a manner that electronic mail including the description contents of both of electronic mail 1 and electronic mail 2 is separately transmitted. It is preferable to give priority to transmission of a message that prompts oil extraction (i.e. contents of electronic mail 1) when a determination that extraction is necessary and a determination that attention needs to be paid are made regarding the same oil.

In the flowchart shown in FIG. 8, the configuration is made in such a manner that the discrimination processing of the abnormality level is repeated until the abnormality level of all pieces of sensor information is determined. However, a configuration may be employed in which, even if the sensor information that has not yet been selected still exists, electronic mail 1 is transmitted and the series of processing is ended once an abnormality determination is made. That is, if an abnormality determination is made in S831, the processing may immediately proceed to S833 and electronic mail 1 may be transmitted, so that the series of processing may be ended. When this configuration is employed, a message that prompts execution of detailed oil analysis can be immediately transmitted if an abnormality determination is made.

Moreover, in the example of FIG. 8, the computer 112 for the administrator and the computer 111 for services are not notified by mail of which determination is made on which kind of sensor information. However, a configuration may be employed in which the computer 112 for the administrator and the computer 111 for services are notified of which determination is made on which kind of sensor information.

Furthermore, for S819 in FIG. 8, the case in which the time change rate of sensor information per one day is a predetermined value (1%, 0.5%) is described. However, this time change rate may be calculated from the time series of this sensor information. Moreover, the time change rate per predetermined time may be utilized instead of the time change rate per one day.

According to the diagnostic system configured as above, even before periodic replacement of oil (period between two times of oil periodic replacement), the user and the person in charge of services regarding the hydraulic excavator 501 can be immediately prompted to extract the oil at a stage when an abnormality or a symptom thereof is found in an oil property (stage when abnormality determination or warning determination is made). This can avoid the occurrence of a situation in which the abnormality progresses by the timing of the next oil periodic replacement. Furthermore, the progression of damage of a part to such an extent that repair is difficult can also be avoided. Therefore, it also becomes easy to apply repair to this part and reuse the part as a reworked part. When expensive parts are used in the work machine, reduction in the running cost due to the use of the reworked parts becomes particularly remarkable.

Furthermore, according to the above-described embodiment, the timing when an oil property becomes abnormal can be predicted and thus it becomes possible to prepare a replacement part or the like in advance in accordance with the predicted timing. Therefore, efficiency improvement and speeding-up relating to maintenance services can be achieved and it becomes possible to shorten downtime of the work machine as much as possible. Furthermore, if the predicted timing is further away (in the future) relative to periodic replacement, it is also possible to postpone the periodic replacement timing from the original plan and thereby reduce downtime of the hydraulic excavator 501.

Modification Example

In the above-described example, the state discriminating section 201 determines the degree of abnormality level of oil based on the magnitude of the sensor information selected in S801 and the abnormality degree determination values (warning determination value and abnormality determination value) (S805, 813). However, instead of this, the difference value between the selected sensor information and sensor information when the oil property relating to this sensor information is sensed in unused oil (initial value of sensor information (oil property information)) may be calculated by the difference value calculating section 207, and this difference value and predetermined abnormality degree determination values (abnormality degree determination values for difference value) may be compared in the state discriminating section 201 to determine the degree of abnormality level of oil. This is because of the following reason.

In carrying out the determination of the abnormality level in the state discriminating section 201, generally the oil property of unused oil (initial value of the oil property) frequently takes a different value depending on the kind of oil, the manufacturer, and so forth. Furthermore, in association with this, the output value of the oil property sensor that senses the property of the unused oil (initial value of sensor information) also differs. However, in many cases, the change amount itself of the oil property does not depend on the kind of oil and the manufacturer comparatively and shows a similar change amount. Therefore, if the degree of abnormality level is determined based on the difference value in this manner, the degree of abnormality level can be determined with the same abnormality degree determination values even when the kind of oil, the manufacturer, and so forth are different.

Furthermore, in the discrimination of the degree of abnormality level of oil, difference may be made depending on whether the accumulation amount of past data is large or small regarding whether sensor information is directly used or the difference value is used. Specifically, if sufficient information has been already obtained regarding the sensor information used for the discrimination, the discrimination based on not the latter (difference value) but the direct value of the former is also possible. However, if the accumulation amount of data on new oil and so forth is small, the evaluation with higher reliability is frequently obtained when the discrimination based on the difference value is carried out. In carrying out discrimination by the state discriminating section 201, in view of the above, the difference value calculating section 207 may be provided and calculation of the change amount may be performed by using the difference value calculating section 207 to carry out the determination if the accumulation amount of data is small.

Of course, it is important to experimentally obtain the correlation between oil properties and sensor information in advance for each kind of oil as the target of evaluation, and generally it is desirable to grasp the basic output values of oil property sensors by using oil in several kinds of states obtained by adjusting the oil properties in advance. Furthermore, the abnormality degree determination values (abnormality determination value and warning determination value) when the "difference value" is used are different from the values in the example of FIG. 8 and are values corresponding to the "difference value." However, the point that the abnormality degree determination values can be decided from past track record values for each oil property (difference of sensor information) stays unchanged, and the outline of the processing is the same as that of FIG. 8. Thus, description of concrete processing when the "difference value" is used is omitted. Furthermore, the abnormality degree determination values may be decided based on one certain threshold as in the already-explained example.

Furthermore, although the degree of abnormality level is determined by using the difference value from the initial value of sensor information here, the degree of abnormality level may be determined by using the difference value from a predetermined value set in advance in place of the initial value of sensor information.

Second Embodiment

Figure 9:
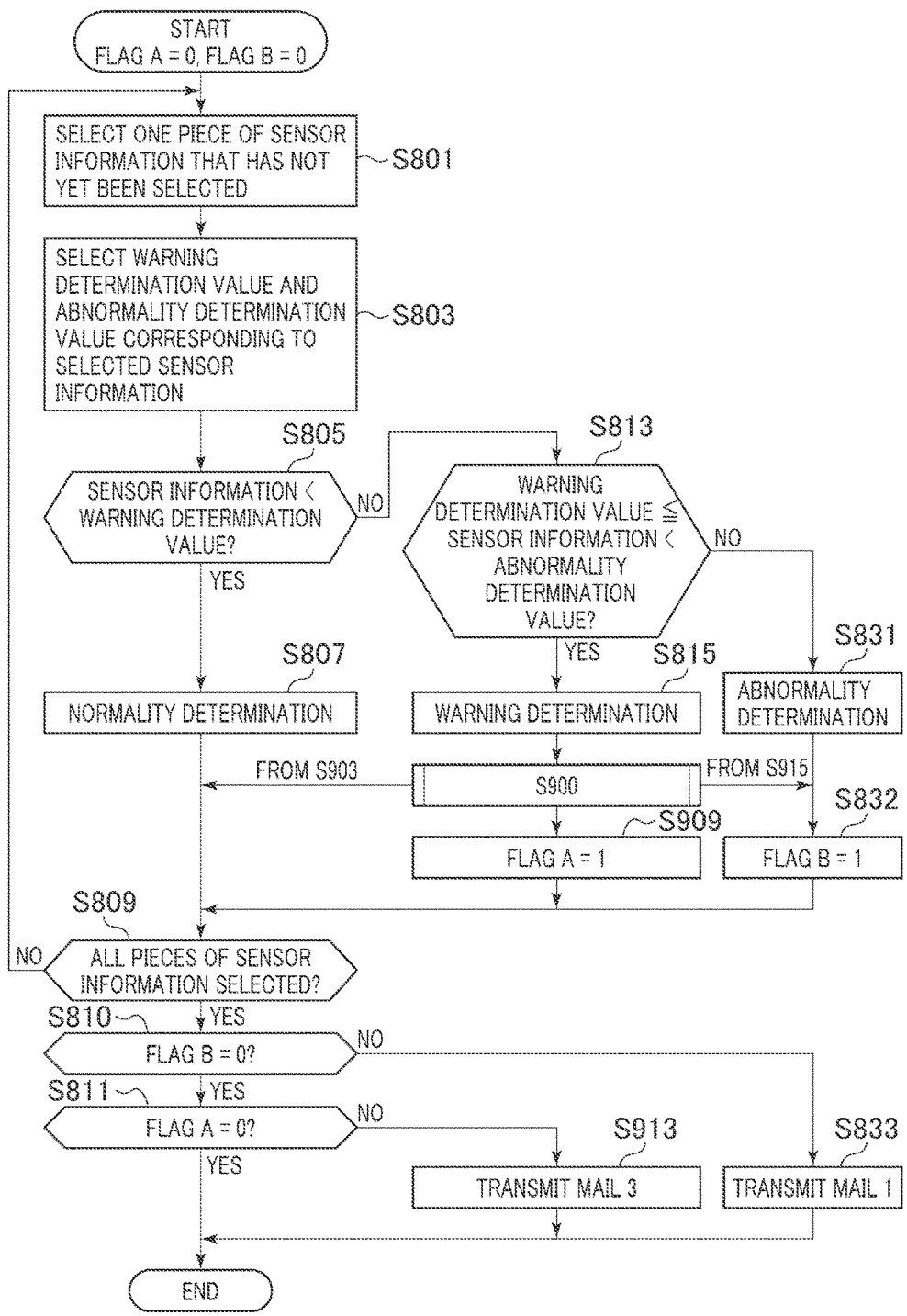
FIG. 9 is one example of a flowchart of processing executed by the computer 110 for the server in a second embodiment.

Next, another example of the series of processing executed by the diagnostic system configured as above will be described by using FIG. 9. FIG. 9 is one example of the flowchart of processing executed by the computer 110 for the server in a second embodiment. Similarly to the processing of FIG. 8, the computer 110 for the server calls the processing of the flowchart of FIG. 9 at a predetermined time interval (call cycle). The same processing as FIG. 8 is given the same numeral and description of the same processing is often omitted.

In the flowchart of FIG. 9, the processing of S801 to S811 and the processing of S831 to S833 are the same as that in FIG. 8. Therefore, processing (S900) subsequent to S815, in which a warning determination is made, will be mainly described here.

Figure 10:
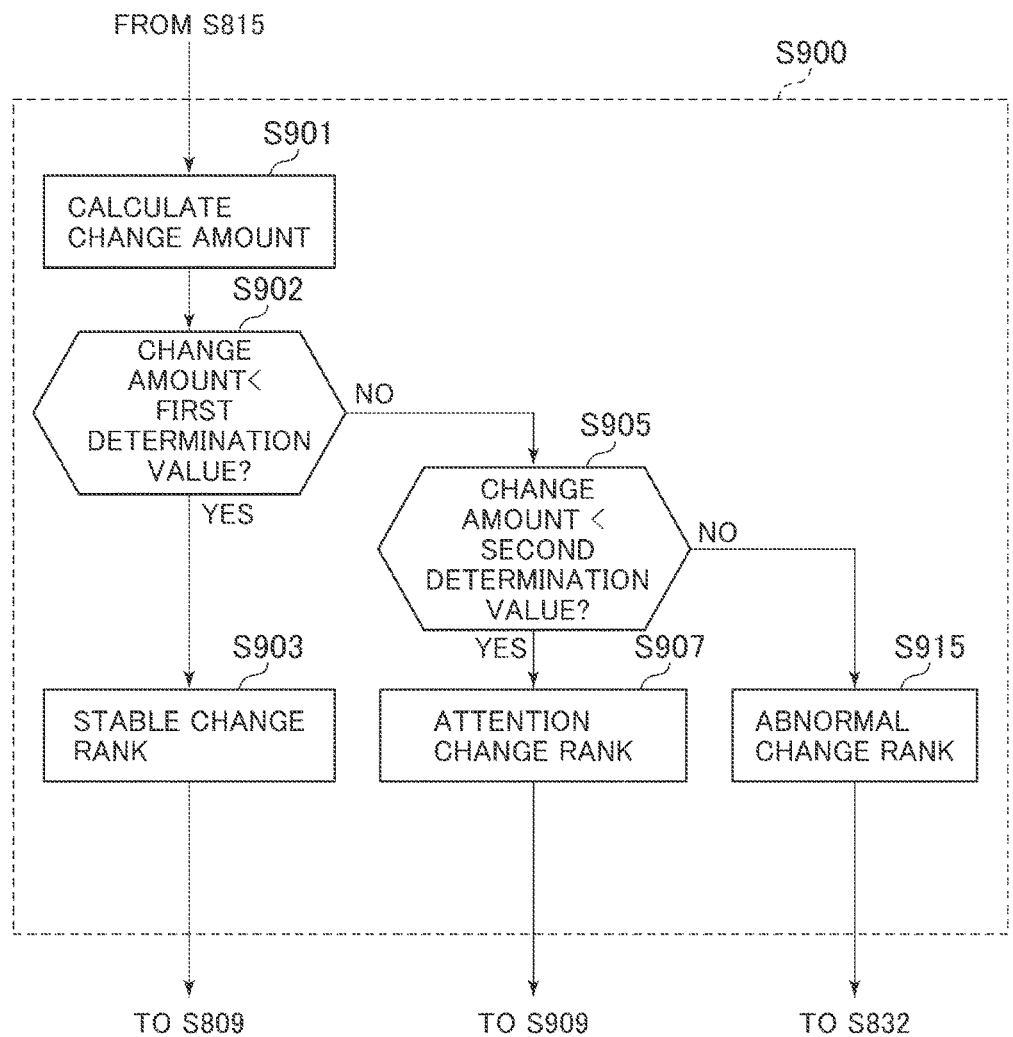
FIG. 10 is a detail chart of processing executed in S900 in FIG. 9.

FIG. 10 is a diagram showing details of the processing executed in S900. If a warning determination is made in S815, the change amount calculating section 204 calculates a change amount that is the difference between the previous value of the sensor information selected and transformed in S801 (sensor information at the time of the previous flowchart call) and the present value (sensor information at the time of the present flowchart call) (S901). The change amount is calculated as the difference between the previous value f(n−1) and the present value f(n), and the change rank determining section 205 ranks the degree of change by comparing this value (f(n)−f(n−1)) and change amount determination values.

The change amount determination values used by the change rank determining section 205 for the ranking are decided based on the oil analysis information of each oil property (sensor information of the second level) that is provided from the oil analysis company and is stored in the data storage device 210 of the computer 104 for the server, i.e. the track record value of the past change amount. The present embodiment uses a first change amount determination value for determining whether or not the change amount calculated in S901 is equivalent to the past change amount and a second change amount determination value for determining that the degree of abnormality level of oil is predicted to early reach the "abnormality determination" because the change amount calculated in S901 is very large. A change in a step function manner or a rapid change in a quadratic function manner or exponential function manner often appears in the sensor information due to any abnormality such as entry of water into oil or entry of dust or the like. The second change amount determination value is set to sense this kind of change. As a result, the second change amount determination value is set to a value larger than the first change amount determination value. Furthermore, an error in measurement of each sensor often appears in the change amount. Thus, in deciding the first change amount determination value and the second change amount determination value, it is preferable to decide them in such a manner that an erroneous determination is not made even when this kind of error occurs.

In S902, the change rank determining section 205 determines whether or not the change amount calculated in S901 is smaller than the first change amount determination value. If the change amount is smaller than the first change amount determination value here, the change rank determining section 205 regards the change amount as equivalent to the past change amount. Furthermore, the change rank determining section 205 deems that there is enough time until the sensor information reaches the level of the "abnormality determination," and classifies the rank of the degree of change into a "stable change rank" (S903). Then, the processing proceeds to S809 in FIG. 9.

On the other hand, if it is determined that the change amount is equal to or larger than the first change amount determination value in S902, the change rank determining section 205 determines whether or not this change amount is smaller than the second change amount determination value (S905). If it is determined that the change amount is equal to or larger than the second change amount determination value here, the change rank determining section 205 deems that the sensor information early surpasses the level of the "abnormality determination," and classifies the rank of the degree of change into an "abnormal change rank" (S915). Then, the processing proceeds to S832 in FIG. 9 and flag B of the abnormality determination is activated (flag B=1 is set). Then, the processing proceeds to S809.

If it is determined that the change amount is smaller than the second change amount determination value in S905, the change rank determining section 205 deems that attention is necessary because the change amount surpasses the past change amount although being not such a value that the sensor information early reaches an abnormality, and classifies the rank of the degree of change into an "attention change rank" (S907). Then, the processing proceeds to S909 in FIG. 9 and flag A is activated (flag A=1 is set (if flag is already 1, it is left as it is)). Then, the processing proceeds to S809.

In S809, it is determined whether or not all pieces of sensor information have been selected. If sensor information that has not yet been selected exists, the processing returns to S801. On the other hand, if all pieces of sensor information have been selected, transition to S810 is made and the extraction timing informing section 203 checks flag B.

If it proves that 0 is set in flag B in the check of flag B in S810, subsequently the extraction timing informing section 203 checks flag A (S811). If it proves that 1 is set in flag A in this check, the extraction timing informing section 203 transmits electronic mail 3 to the computer 112 for the administrator and the computer 111 for services (S913), and the series of processing is ended. In electronic mail 3, for example a message of "Please pay attention to the determination of the sensor output result in the future because the abnormality level of oil has surpassed the warning determination level" or the like is described. Thereby, related persons of the hydraulic excavator 501 are prompted to pay attention.

According to the system configured as described above, determination can be carried out regarding whether the necessity to carry out detailed oil analysis involving oil extraction exists also in consideration of the change amount. Therefore, it is possible to prompt related persons of the hydraulic excavator 501 to extract oil also in the case in which the time to the next oil periodic replacement is unclear when a warning determination is made.

In the above-described example, the configuration is employed in which electronic mail 3 is transmitted when the rank of the degree of change is classified into the "attention change rank." However, the necessity to carry out oil replacement, a check of equipment, or the like as soon as possible does not exist as long as the sensor information is lower than the abnormality determination value. Therefore, a configuration in which nothing is especially done similarly to the case of the "stable change rank" may be employed. Furthermore, instead of this, a configuration in which electronic mail in which a message of "an abnormality does not exist" or the like is described is transmitted may be employed. Moreover, operation may be carried out in which, even if electronic mail is transmitted, transmission to the computer 112 for the administrator is omitted and the electronic mail is transmitted only to the computer for services (agency or the like).

Furthermore, in the above-described example, whether or not the necessity for oil extraction exists is determined based on the change amount only when a warning determination is made. However, whether or not the necessity for oil extraction exists may be determined based on the change amount also when a normality determination is made. Moreover, in the above, the difference between the previous value and the present value of sensor information is employed as the change amount. However, the difference between an older value than the previous value (i.e. sensor information that is previous by at least two times of processing) and the present value may be employed as the change amount.

Third Embodiment

The present embodiment has a characteristic in that, when a determination that oil extraction is necessary is made based on sensor information input from the sensor group 101, the cause of the determination is also identified by using the abnormality cause identifying section 208 (see FIG. 5) of the computer 104 for the server. If a determination that oil extraction is necessary is made, the abnormality cause identifying section 208 executes processing of identifying the cause of the abnormality of the oil based on the sensor information as the basis of the determination and past oil analysis information of the oil property relating to this sensor information.

The abnormality cause identifying section 208 of the present embodiment identifies the cause of an abnormality based on values (evaluation values) obtained by transforming the respective pieces of sensor information from the sensor group 101 through predetermined expressions (evaluation formulas). The evaluation formulas exist corresponding to the number of oil properties sensed by the sensor group 101 (i.e. the number of kinds of sensor information), and each evaluation formula is created based on past sensor information and oil analysis information of a certain oil property. The evaluation value is calculated when sensor information from an arbitrary sensor included in the sensor group 101 is input to the evaluation formula corresponding thereto. The evaluation value is ranked based on at least one rank determination value set in advance for each evaluation value (each oil property) and the cause of an abnormality is identified based on the rank of each evaluation value (each oil property).

The relationship between the rank determination value and the rank will be mentioned. For example, if one rank determination value is set for a certain evaluation value (certain oil property), this evaluation value is classified into two ranks. If the number of rank determination values is two, the evaluation value is classified into three ranks.

The cause of an abnormality is not only identified based on the rank of one evaluation value but identified also based on a combination of the ranks of at least two evaluation values (refer to an example of "mixing of dust or wear debris" to be described later). The combination of the cause of an abnormality and the rank of at least one evaluation value corresponding thereto is set in advance.

Figure 11:
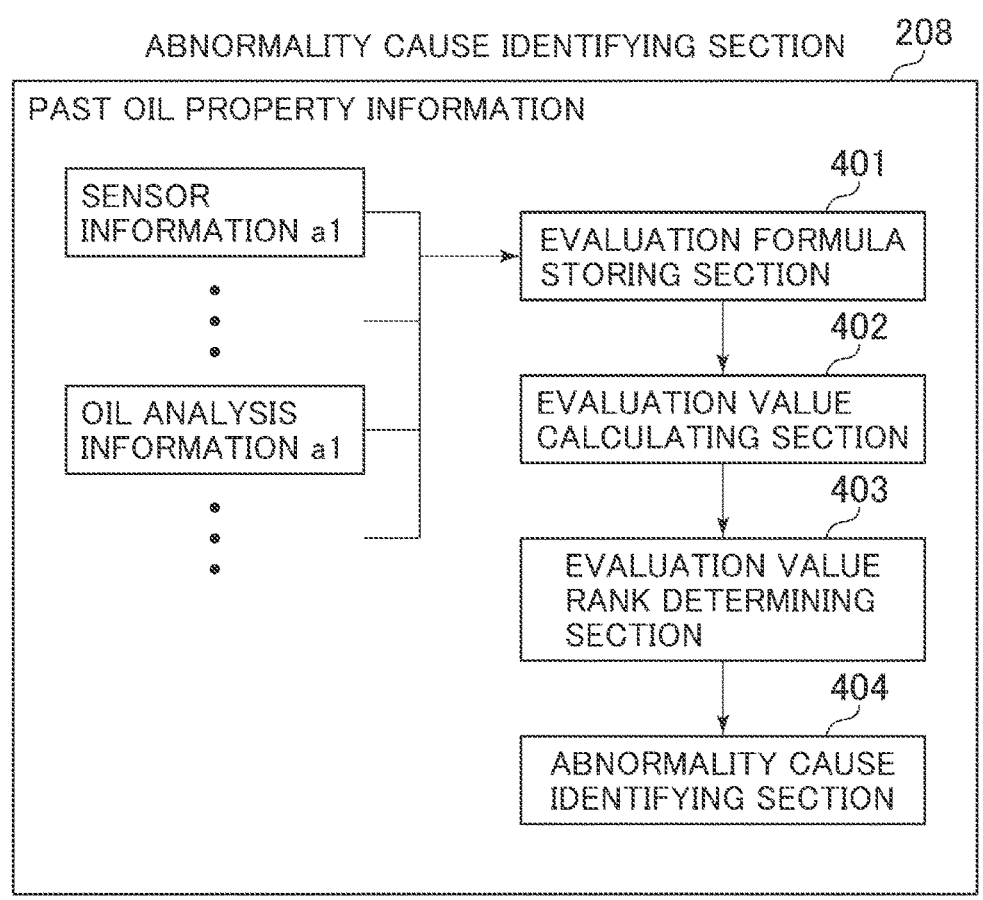
FIG. 11 is a schematic configuration diagram of an abnormality cause identifying section 208 according to a third embodiment.

FIG. 11 is a schematic configuration diagram of the abnormality cause identifying section 208 according to the present embodiment. As shown in this diagram, the abnormality cause identifying section 208 includes an evaluation formula storing section 401, an evaluation value calculating section 402, an evaluation value rank determining section 403, and an abnormality cause identifying section 404.

In the evaluation formula storing section 401, the evaluation formulas corresponding to the oil properties sensed by the sensor group 101 are stored. Normally plural properties exist as the oil properties sensed by the sensor group 101. Thus, also as for the evaluation formulas, the same number of formulas as the oil properties exist, i.e. plural formulas exist.

The evaluation value calculating section 402 is a section that executes processing of seeking the evaluation formula corresponding to sensor information (oil property) input from the sensor group 101 from the evaluation formula storing section 401 and inputting the sensor information into the sought evaluation formula to calculate the evaluation value.

In the present embodiment, the following expression, (expression 2), is employed as the evaluation formula. In expression 2, $\Delta X_i(t)$ is what is obtained by representing the measurement value $X_i(t)$ (see expression 1) obtained by transforming sensor information of a certain oil property into a value in a predetermined temperature range based on the ratio with respect to the initial value thereof (referred to as "measurement value change rate"). $\Delta Y_j(t)$ is the evaluation value and here is what is obtained by representing oil analysis information of the oil property corresponding to $\Delta X_i(t)$ based on the ratio with respect to the initial value thereof (referred to as "analysis value change rate"). $b_{0j}$ represents a constant term of an explanatory variable i for an evaluation item j and $b_{ij}$ represents a partial regression coefficient of the explanatory variable i for the evaluation item j. The constant term $b_{0j}$ and the partial regression coefficient $b_{ij}$ can be decided by carrying out a multiple regression analysis based on past values of sensor information and oil analysis information about a respective one of oil properties regarding the correlation between the measurement value change rate $\Delta X_i(t)$ and the analysis value change rate $\Delta Y_j(t)$.

$$\Delta Y_j(t) = b_{0j} + \Sigma b_{ij} \cdot \Delta X_i(t) \quad \text{(expression 2)}$$

The evaluation value rank determining section 403 is a section that executes processing of classifying the rank of the evaluation value based on the evaluation value calculated in the evaluation value calculating section 402 and the rank determination value of this evaluation value. Here, the rank is represented by an integer. Rank 0 is the rank serving as the basis (rank of the initial value). The rank increases to rank 1, 2, 3 . . . in association with the increase in the evaluation value and decreases to rank −1, −2, −3 . . . in association with the decrease in the evaluation value. As already described, the number of ranks relating to a certain evaluation value (certain oil property) depends on the number of rank determination values. For example, if three ranks of rank −1, rank 0, and rank 1 exist regarding the viscosity ($\Delta Y_1$), the number of rank determination values is two. As the evaluation value (oil property), the following evaluation values exist: (1) evaluation value having only positive ranks besides rank 0 (i.e. evaluation value that only increases from the initial value over time); (2) evaluation value having only negative ranks besides rank 0 (i.e. evaluation value that only decreases from the initial value over time); and (3) evaluation value having both positive and negative ranks besides rank 0 (i.e. evaluation value having a possibility of increase and decrease from the initial value, and the above-described example of the viscosity ($\Delta Y_1$) corresponds thereto).

The abnormality cause identifying section 404 identifies the cause of an abnormality based on the ranks of the respective evaluation values classified in the evaluation value rank determining section 403. For example, regarding the viscosity ($\Delta Y_1$), "oil deterioration" is set as the cause in the case of rank 1 and "fuel mixing" is set as the cause in the case of rank −1. Furthermore, if the rank of the viscosity ($\Delta Y_1$) is determined to be 1 in the evaluation value rank determining section 403, the abnormality cause identifying section 404 outputs "oil deterioration" as the cause of an abnormality. Moreover, in the case in which "mixing of dust or wear debris" is set as the cause of rank 1 for the viscosity ($\Delta Y_1$) and rank 1 for the dielectric constant ($\Delta Y_3$), the abnormality cause identifying section 404 outputs "mixing of dust or wear debris" as the cause of an abnormality when the viscosity ($\Delta Y_1$) and the dielectric constant ($\Delta Y_3$) are each determined to be at rank 1 in the evaluation value rank determining section 403.

The cause of an abnormality identified by the abnormality cause identifying section 208 in the above described manner is transmitted with the abnormal item to at least one of the computer 110 for the work machine, the computer 111 for services, and the computer 112 for the administrator together with or separately from the oil extraction request 301, and a proper response corresponding to the cause of the abnormality is carried out by related persons in order to achieve elimination of the abnormality.

According to the present embodiment, it becomes possible to identify the cause of an abnormality of oil based on sensor information of the sensor group 101. Due to this, for example if an increase in the amount of mixing of wear debris of metal components into oil is identified as the cause of an abnormality, an overhaul check of equipment as a countermeasure against the cause can be early prompted. Thus, efficiency improvement of the check work can be achieved and the countermeasure (for example, part replacement) can be carried out, with the abnormality kept minimal. Furthermore, for example if an abnormality occurs when the hydraulic excavator 501 is used at a remote place from a manufacturer agency and it is predicted that the abnormality is turned to the normal state only by carrying out part replacement (for example, oil replacement or filter replacement), a person in charge of services can go off to the hydraulic excavator 501 while bringing the relevant replacement part in advance. Thus, efficiency improvement and speeding-up relating to maintenance services can be achieved. Furthermore, depending on the case (for example, if easy part replacement that can be sufficiently handled even by a user is requested), it is also possible to eliminate the abnormality without waiting for the arrival of a person in charge of services through transmission of the coping method 302 by the person in charge of services from the computer 111 for services to the computer 112 for the administrator instead of going off to the hydraulic excavator 501 and execution of the part replacement by the user oneself. As above, according to the present embodiment, reduction in the expenses for services and the parts replacement cost as the total lifecycle cost can be achieved. In addition, downtime of the work machine can be shortened and it also becomes possible to improve the utilization rate.

In the above, description is made by taking as an example the connection form in which the computer 110 for the work machine and the computer 104 for the server can always carry out data communications in order to implement real-time abnormality monitoring. However, operation may be carried out in which pieces of sensor information accumulated in the computer 110 for the work machine are periodically output to an external memory (for example, USB flash memory) and the data of the external memory is output to the computer 104 for the server.

The present invention is not limited to the above-described respective embodiments and various modification examples in such a range as not to depart from the gist of the present invention are included. For example, the present invention is not limited to what includes all configurations explained in the above-described embodiment and what is obtained by removing part of the configurations is also included. Furthermore, it is possible that part of a configuration according to a certain embodiment be added to or replaced by a configuration according to another embodiment.

Furthermore, part or all of the respective configurations relating to the above-described computers and functions, executed processing, and so forth of these respective configurations may be implemented by hardware (for example, designing logic to execute the respective functions by an integrated circuit, or the like). Furthermore, the configurations relating to the above-described computers may be a program (software) that is read out and executed by an arithmetic processing device (for example, central processing unit (CPU)) to implement the respective functions relating to the configurations of these computers. Information relating to this program can be stored in a semiconductor memory (flash memory, solid state drive (SSD), and so forth), a magnetic storage device (hard disk drive and so forth), a recording medium (magnetic disc, optical disc, and so forth), and so forth for example.

Furthermore, in the explanation of the above-described respective embodiments, lines interpreted as necessary for the explanation are shown as control lines and information lines. However, all control lines and information lines relating to products are not necessarily shown. It may be deemed that actually almost all configurations are mutually connected.

DESCRIPTION OF REFERENCE CHARACTERS

101 . . . Sensor group, 101A, 101B, 101C . . . Sensor, 102 . . . Sensor information, 104 . . . Computer for server, 110 . . . Computer for work machine, 111 . . . Computer for services, 112 . . . Computer for administrator, 113 . . . Computer for analysis company, 201 . . . State discriminating section, 202 . . . Extraction necessity determining section, 203 . . . Extraction timing informing section, 204 . . . Change amount calculating section, 205 . . . Change rank determining section, 206 . . . Abnormal part identifying section, 207 . . . Difference value calculating section, 208 . . . Abnormality cause identifying section, 210 . . . Data storage device, 301 . . . Oil extraction request, 303 . . . Analysis result, 304 . . . Analysis-diagnosis result, 401 . . . Evaluation formula storing section, 402 . . . Evaluation value calculating section, 403 . . . Evaluation value rank determining section, 404 . . . Abnormality cause identifying section, 501 . . . Hydraulic excavator

The invention claimed is:

1. A diagnostic system for a work machine including a server computer that collects at least one piece of sensor information from at least one oil property sensor provided in the work machine and determines an abnormality of the work machine based on the at least one piece of sensor information, the at least one oil property sensor sensing at least one oil property about oil used for operation of the work machine, comprising:
a data storage device in which the at least one piece of sensor information input from the at least one oil property sensor at least one determination value defined for each kind of the at least one piece of sensor information are stored;
a processor connected to a memory storing instructions that when executed by the process configure the processor to: determine a degree of abnormality level of the oil based on the at least one piece of sensor information and the at least one determination value relating to the at least one piece of sensor information,
determine whether the degree of abnormality level of the oil progresses to such an extent that an oil analysis involving oil extraction is necessary if the work machine is operated until a timing of a next oil replacement based on the determined degree of abnormality level of the oil the at least one piece of sensor information and a time change rate of the at least one piece of sensor information, and
output information indicating that the oil analysis involving oil extraction is necessary to a computer connected to the server upon determining that the oil analysis involving oil extraction is necessary.

2. The diagnostic system for a work machine according to claim 1, wherein
the processor is configured to calculate a difference value between the at least one piece of sensor information and a predetermined value corresponding to the at least one piece of sensor information and determine the degree of abnormality level of the oil based on the difference value and a determination value relating to the difference value.

3. The diagnostic system for a work machine according to claim 1, wherein
the processor is configured to, upon determining that the oil analysis involving oil extraction is necessary identify a cause of an abnormality of the oil based on sensor information as a basis of the determination and past oil analysis information of the oil property relating to the sensor information as the basis of the determination.

4. The diagnostic system for a work machine according to claim 1, wherein
the processor is configured to, upon determining that the oil analysis involving oil extraction is necessary identify a part in which an abnormality exists based on a setting place of the sensor that has output the sensor information as a basis of the determination.

5. A diagnostic system, comprising:
a work machine including at least one oil property sensor sensing at least one oil property about oil used for operation of the work machine; and
a server computer including:
a data storage device in which the at least one piece of sensor information input from the at least one oil property sensor and at least one determination value defined for each kind of the at least one piece of sensor information are stored;
a processor connected to a memory storing instructions that when executed by the process configure the processor to:
determine a degree of abnormality level of the oil based on the at least one piece of sensor information and the at least one determination value relating to the at least one piece of sensor information,
determine whether the degree of abnormality level of the oil progresses to such an extent that an oil analysis involving oil extraction is necessary if the work machine is operated until a timing of a next oil replacement based on the determined degree of abnormality level of the oil the at least one piece of sensor information and a time change rate of the at least one piece of sensor information, and
output information indicating that the oil analysis involving oil extraction is necessary to a computer connected to the server upon determining that the oil analysis involving oil extraction is necessary.

* * * * *